(12) United States Patent
Fogarty et al.

(10) Patent No.: US 7,706,985 B2
(45) Date of Patent: Apr. 27, 2010

(54) SYSTEM AND METHOD FOR IN-SITU MONITORING OF COMPOSITE MATERIALS

(75) Inventors: Michael D. Fogarty, Auburn, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/818,702

(22) Filed: Jun. 15, 2007

(65) Prior Publication Data

US 2008/0312848 A1 Dec. 18, 2008

(51) Int. Cl.
G01B 5/28 (2006.01)
G01H 13/00 (2006.01)
G01N 29/04 (2006.01)

(52) U.S. Cl. ............................. 702/39; 702/33; 73/598; 73/628; 73/582

(58) Field of Classification Search ................... 73/628, 73/598, 582; 702/39, 33
See application file for complete search history.

(56) References Cited

U.S. PATENT DOCUMENTS

| | | | | |
|---|---|---|---|---|
| 4,184,373 A * | 1/1980 | Evans et al. | ................... | 73/588 |
| 4,538,462 A * | 9/1985 | Hartog et al. | ................. | 73/577 |
| 5,072,611 A * | 12/1991 | Budd et al. | ............. | 73/115.07 |
| 5,735,282 A * | 4/1998 | Hossack | ..................... | 600/458 |
| 6,484,583 B1 * | 11/2002 | Chennell et al. | .............. | 73/623 |
| 6,532,820 B1 * | 3/2003 | Fleming et al. | ............... | 73/627 |
| 6,945,111 B2 * | 9/2005 | Georgeson | ................... | 73/600 |
| 2004/0139801 A1 * | 7/2004 | Wilk | ........................... | 73/627 |
| 2005/0217388 A1 * | 10/2005 | Heyman et al. | ................ | 73/827 |
| 2006/0179949 A1 * | 8/2006 | Kim | ............................ | 73/588 |
| 2006/0259217 A1 * | 11/2006 | Gorinevsky et al. | ........... | 701/29 |
| 2007/0017297 A1 | 1/2007 | Georgeson et al. | | |

OTHER PUBLICATIONS

Gyekenyesi et al., In Situ Monitoring of Damage in SiC/SiC Composites Using Acousto-Ultrasonics, Composites Part B: Engineering, Elsevier, vol. 37, No. 1, Jan. 1, 2006.
Reynolds et al., Nondestructive Testing (NDT) of Fibre-Reinforced Composite Materials, Materials and Design, London, vol. 5, No. 6, Dec. 1, 1984.
International-Search Report Written Opinion of International Searching Authority, International Application No. PCT/US2008/067014, Oct. 2, 2008.

* cited by examiner

*Primary Examiner*—Eliseo Ramos Feliciano
*Assistant Examiner*—Janet L Suglo
(74) *Attorney, Agent, or Firm*—Toler Law Group (57) ABSTRACT

In a non-limiting, exemplary system for in-situ monitoring of a composite workpiece, at least one ultrasonic testing transducer is mounted to a surface of a composite workpiece and configured to transmit and receive ultrasonic energy to and from the composite workpiece during mechanical loading of the composite workpiece. An ultrasonic pulser/receiver is operatively coupled to the at least one ultrasonic testing transducer. A computing system is operatively coupled to the ultrasonic pulser/receiver. The computing system includes a data acquisition component configured to acquire data from the ultrasonic pulser/receiver and a data analysis component configured to analyze the acquired data. The data analysis component may be further configured to analyze the acquired data for initiation of failure of the composite workpiece and/or growth of failure of the composite workpiece. Further, failure of the composite workpiece may include cracking and/or delaminating and/or disbonding.

29 Claims, 7 Drawing Sheets

SYSTEM AND METHOD FOR IN-SITU MONITORING OF COMPOSITE MATERIALS

BACKGROUND

Various parts and structures are currently designed and built using composites, many of which are bonded together using adhesives. The study of bonded and co-cured composite interface behavior under load is important to the proper design and use of these structures. For example, structural analysis codes are used to predict locations and load levels for failure initiation. Composite manufacturers and manufacturers of structures using composites employ various mechanical testing machines to stress representative composites to failure in order to validate and refine structural performance codes.

Accurately defining the onset of structural failure would be desirable for generating structural analysis codes. However, currently it is not possible to determine the initiation of failure due to the start of a disbond or delamination or cracking from the load-displacement curve produced during mechanical testing (such as bending, tension, compression, and the like). For example, there is no "knee" in the curve that would indicate that a structure has begun to fail. Crack wires and conductive paint can sometimes be used in cases where a delamination initiates at a re-entrant corner, but they cannot be used to detect growth from an internal feature or an existing internal delamination. Many times, test engineers cannot verify where damage is initiating or growing.

In addition, currently a non-destructive inspection (NDI) technician or other operator is required to periodically inspect locations of a structure under test. In such cases, testing has to be stopped (that is, the load is removed from the structure under test) for personnel safety purposes. This is because an operator currently must hold an ultrasonic testing (UT) transducer in place to inspect the unit. However, for personnel safety reasons, an operator can not hold a transducer onto a structure while load is being applied to the structure. Therefore, currently load is removed from the structure, the operator places the transducer on the structure, and the unloaded structure is then inspected. This process can mean that a high-use test machine, possibly with a backlog of testing, may sit idle while waiting for a shift change so the NDI technician can check for cracking or delamination or disbond growth. Moreover, the precision of the dimensional measurement is limited by the damage marking precision (to define the physical extent of the damage) and the technician's ability to discern small changes.

Therefore, improvements may be possible regarding increases in sensitivity, accuracy, and repeatability of measurement data, regarding determining the initiation of failure, and regarding reductions in schedule and labor costs.

The foregoing examples of related art and limitations associated therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems and methods which are meant to be exemplary and illustrative, not limiting in scope. In various embodiments, one or more of the problems described above in the Background have been reduced or eliminated, while other embodiments are directed to other improvements.

In a non-limiting, exemplary system for in-situ monitoring of a composite workpiece, at least one ultrasonic testing transducer is mounted to a surface of a composite workpiece and configured to transmit and receive ultrasonic energy to and from the composite workpiece during mechanical loading of the composite workpiece. An ultrasonic pulser/receiver is operatively coupled to the at least one ultrasonic testing transducer. A computing system is operatively coupled to the ultrasonic pulser/receiver. The computing system includes a data acquisition component configured to acquire data from the ultrasonic pulser/receiver and a data analysis component configured to analyze the acquired data.

According to an aspect, the data analysis component may be further configured to analyze the acquired data for initiation of failure of the composite workpiece and/or growth of failure of the composite workpiece. Further, failure of the composite workpiece may include cracking and/or delaminating and/or disbonding.

According to another exemplary embodiment, a non-limiting, exemplary system is provided for testing a composite workpiece. A mechanical test system and controller is configured to cause a composite workpiece to be placed under mechanical load. At least one ultrasonic testing transducer is mounted to a surface of the composite workpiece and configured to transmit and receive ultrasonic energy to and from the composite workpiece during mechanical loading of the composite workpiece. An ultrasonic pulser/receiver is operatively coupled to the at least one ultrasonic testing transducer. A computing system is operatively coupled to the mechanical test system and controller and to the ultrasonic pulser/receiver. The computing system includes a data acquisition component configured to acquire data from the ultrasonic pulser/receiver and a data analysis component configured to analyze the acquired data.

According to an aspect, the computing system can further include a control component configured to automatically cause the mechanical test system and controller to stop causing the composite workpiece to be placed under mechanical load responsive to detection by the data analysis component of initiation of failure of the composite workpiece.

In addition to the exemplary embodiments and aspects described above, further embodiments and aspects will become apparent by reference to the drawings and by study of the following detailed description.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Figure 1:
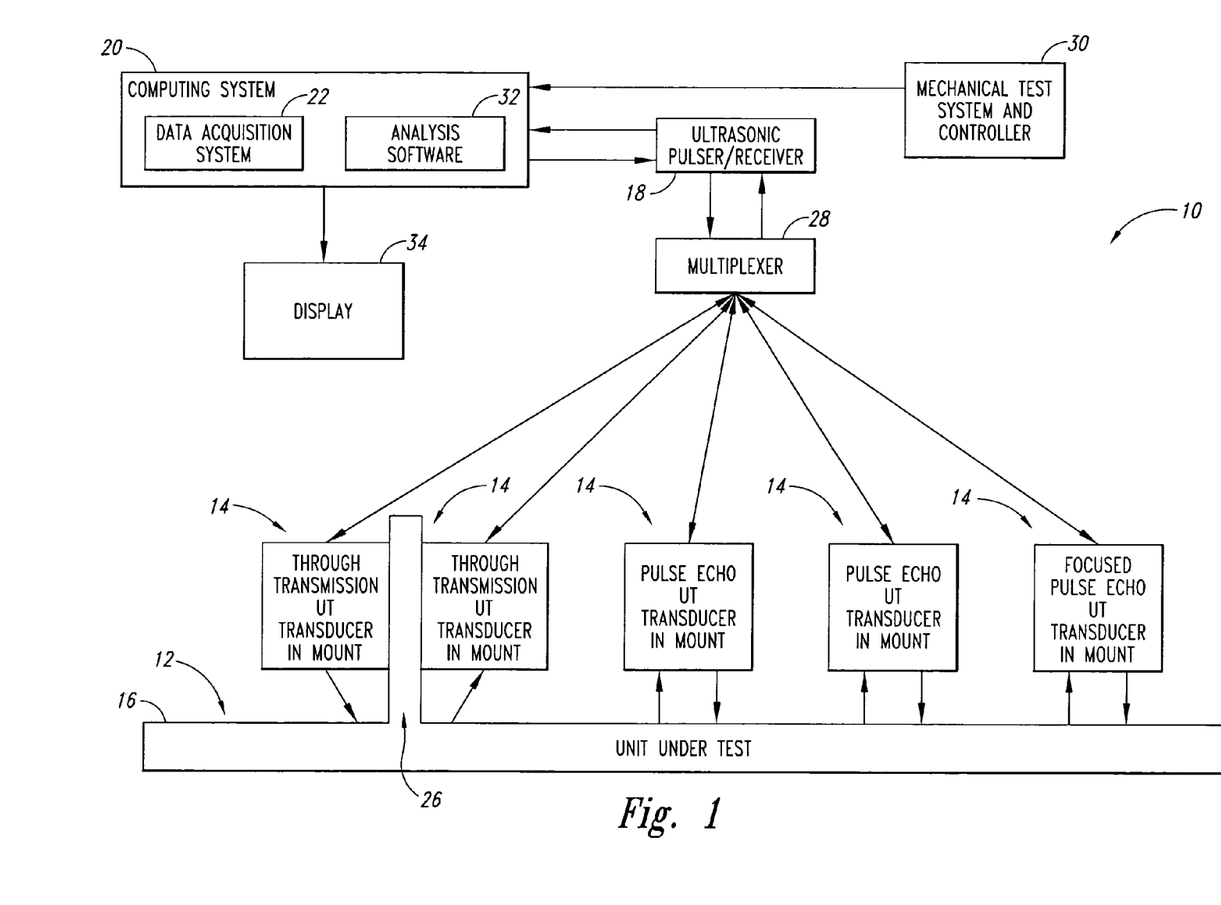
FIG. 1 is a block diagram of an exemplary system for in-situ monitoring of composite materials.

By way of overview and referring to FIG. 1, in a non-limiting, exemplary system 10 for in-situ monitoring of a composite workpiece or unit under test (UUT) 12, at least one ultrasonic testing UT transducer 14 is mounted to a surface 16 of a composite UUT 12 and configured to transmit and receive ultrasonic energy to and from the composite UUT 12 during mechanical loading of the composite UUT 12. An ultrasonic pulser/receiver 18 is operatively coupled to the at least one ultrasonic testing transducer 14. A computing system 20 is operatively coupled to the ultrasonic pulser/receiver 18. The computing system 20 includes a data acquisition component 22 configured to acquire data from the ultrasonic pulser/receiver 18 and a data analysis component 24 configured to analyze the acquired data. Details of exemplary embodiments will now be set forth below.

The UUT 12 suitably is any composite part or structure. For example, the UUT 12 may be a co-cured or bonded composite part or structure. As such, the UUT may include hidden cracks or delaminations. Further, the UUT 12 may include a joint 26.

The UT transducers 14 may be any suitable UT transducer as desired for a particular application. Moreover, any number of the UT transducers 14 may be mounted on the UUT 12 in location and in any arrangement or pattern as desired for a particular application. As an example, because joints represents key areas of interest in composite structures, through transmission UT transducers may be mounted near the joint 26. As another example, several of the UT transducers 14 may be mounted on the surface 16 and arranged in an array, such as a linear array or a matrix array (that is, a two-dimensional array) in order to track growth of failure in the UUT 12. The UT transducers 14 are ultrasonically coupled to the surface 16 by a suitable couplant, such as silicone grease or a column of water or a wave guide or the like. The UT transducer 14 receives electrical energy, converts the electrical energy to a stress wave that is sent into the UUT 12, receives a reflected signal, and converts the reflected signal to an electrical signal.

The UT transducers 14 may be any one or more types of UT transducer as desired. Unlike hand-held transducers used in previously-known composite testing and monitoring performed only after mechanical loading had been stopped, the UT transducers 12 are mounted to the surface 16, thereby permitting ultrasonic testing of the UUT 12 to be performed while the UUT 12 is under mechanical loading. Use of the UT transducers 14 that are mounted to the surface 16 of the UUT 12 thus permits data to be collected that has not been collectible in previously-known ultrasonic testing of composite structures.

Placement and mounting of the UT transducers 14 and resultant acquisition of such previously uncollectible data thus enables improvements over previously known methods to be made regarding increases in sensitivity, accuracy, and repeatability of measurement data, regarding determining the initiation of failure, and regarding reductions in schedule and labor costs. In addition, the UT transducers 14 are mounted to the surface 16 of the UUT 12 and, therefore, an operator need not and does not hold the UT transducers 14 onto the surface 16 of the UUT 12 while the UUT 12 is under mechanical loading. Therefore, such mounting of the UT transducers 12 helps provide for personnel safety while acquiring the previously-uncollectible data while the UUT 12 is under mechanical load.

The UT transducers 14 suitably may be any UT transducer having a size and frequency as desired for a particular purpose. Given by way of non-limiting example and not by way of limitation, some of the UT transducers 14 may have a frequency of around 5 MHz or so for inspection of carbon-reinforced composite structures. In addition, the UT transducers 14 may be pulse echo UT transducers, such as flat beam or focused pulse echo UT transducers, as desired for a particular application. Further, the UT transducers 14 may be through transmission UT transducers as desired for a particular application, such as inspection of a joint.

The UT transducers 14 are mounted to the surface 16 of the UUT 12. exemplary mounts for mounting the UT transducers 14 are disclosed in a concurrently-filed U.S. patent application Publication No. 2008/0307637 the entire contents of which are hereby incorporated by reference. An overview of exemplary mounts for the UT transducers 14 will now be set forth below.

Figure 2A:
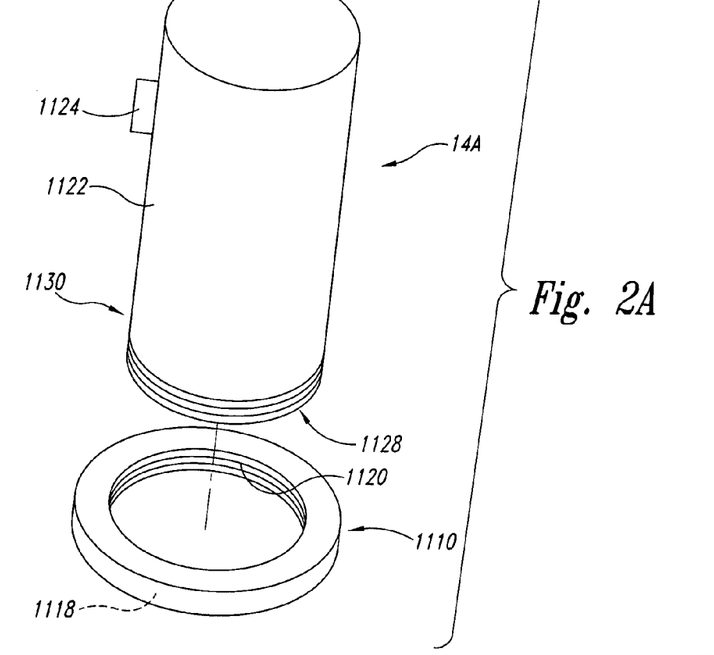
FIG. 2A is an exploded perspective view of an exemplary pulse echo ultrasonic testing transducer and an exemplary surface ring mount.

Referring now to FIG. 2A, a mount assembly 1110 can mount a pulse echo ultrasonic testing (UT) transducer 14A. The mount assembly 1110 may be capable of handling large strains and may be suitable for many applications as desired.

In this non-limiting embodiment, the mount assembly is a surface ring. The surface ring 1110 has a substantially planar surface 1118 arranged to attach the surface ring 1110 to the surface 16. For example, the surface 1118 may be adhered to the surface 16 with a suitable adhesive as desired for a particular application. The surface ring 1110 has a threaded inner surface 1120.

The pulse echo UT transducer 14A suitably has a cylindrical body 1122. An electrical connection port 1124 is provided toward an upper portion 1126 of the cylindrical body 1122. Threads 1128 are defined around the exterior of a lower portion 1130 of the body 1122.

The body 1122 is rotated in the surface ring 1110 so the threads 1120 threadedly engage the threads 1128. When the body 1122 is completely threaded into the surface ring 1110, the pulse echo UT transducer 14A is securely mounted to the UUT 12.

Figure 2B:
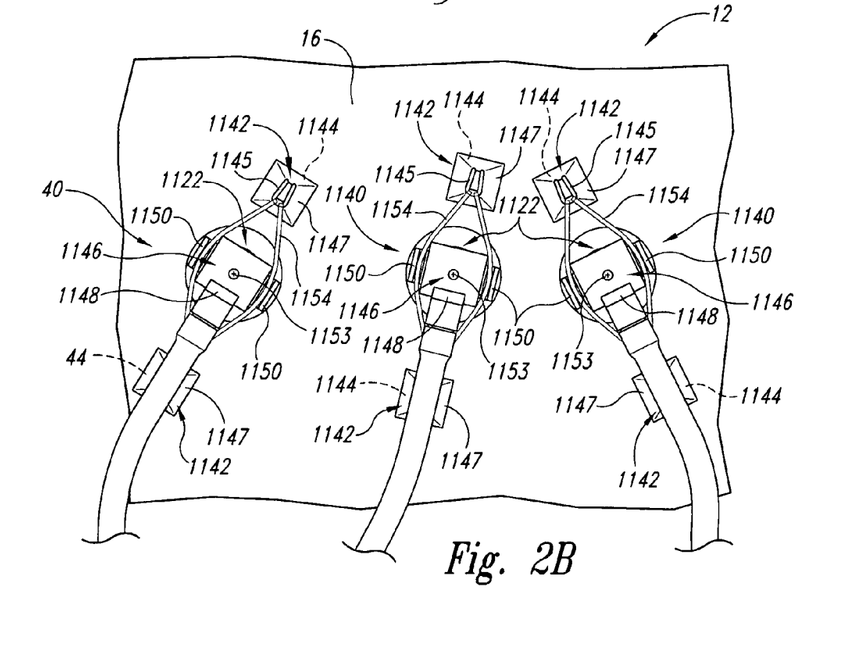
FIG. 2B illustrates exemplary pulse echo ultrasonic testing transducers mounted with an exemplary hold-down cap.

Referring now to FIG. 3A, a mount assembly 1140 can mount a pulse echo UT transducer to the surface 16 of the UUT 12. In one embodiment, the pulse echo UT transducer can be threaded such as the pulse echo UT transducer 14A. In another embodiment, the pulse echo UT transducer need not be threaded. As with the mount assembly 1110 (FIG. 2A), the mount assembly 1140 may be capable of handling large strains.

Attachment pads 1142 each have a surface 1144 arranged to adhere to the surface 16. For example, the surface 1144 may be adhered to the surface 16 with a suitable adhesive as desired for a particular application. Each attachment pad 1142 has an attachment loop 1145 that extends from an upper surface 1147 of the attachment pad 1142.

A hold-down cap 1146 is arranged to receive therein the upper portion 1126 of a pulse echo UT transducer, such as the pulse echo UT transducer 14A (or a pulse echo UT transducer without threads). A cut-out 1148 defined in the hold-down cap 1146 accommodates the electrical connection port 1124, thereby permitting the hold-down cap 1146 to be placed upon the upper portion 1126. Flanges 1150 extend from opposite sides of the hold-down cap 1146. A de-biasing screw 1153 is provided through a hole (not shown) in the center of the top of the hold-down cap 1146. The de-biasing screw 1153 allows the transducer to be driven against the surface 16 by a point source.

A biasing member 1154 is looped through the attachment loops 1145 and is placed onto the flanges 1150, thereby biasing the hold-down cap 1146 against the upper portion 1126 of a pulse echo UT transducer. The biasing member 1154 may be an elastomeric band.

In one embodiment the portion 1130 of the pulse echo UT transducer need not be threaded. In such a case, the surface ring 1110 need not be used with the mounting assembly 1140. The mount assembly 1140 can thus handle large strains as a standalone mount assembly and may be suitable for many applications as desired.

In another embodiment, the portion 1130 of the pulse echo UT transducer is threaded and the surface ring 1110 can be used with the mounting assembly 1140. Use of the surface ring 1110 along with the mounting assembly 1140 can thus provide for redundant attachment to the UUT 14 and can accommodate even larger strains than can either the surface ring 1110 or the mount assembly 1140 alone.

Figure 2C:
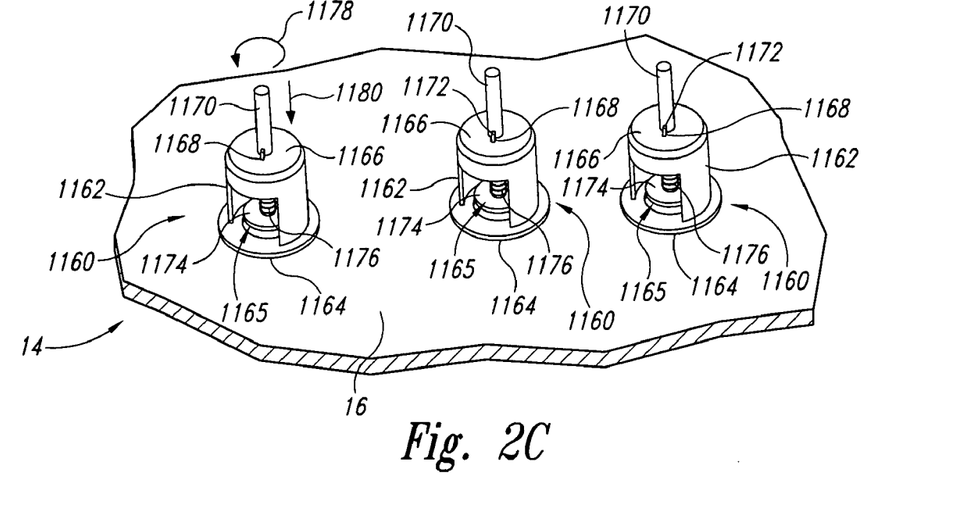
FIG. 2C is a perspective view of exemplary canister mounts for pulse echo ultrasonic testing transducers.

Referring now to FIG. 2C, a mount assembly 1160 can mount a pulse echo UT transducer to the surface 16 of the UUT 12. The mount assembly 1160 can be used where space is limited or where interference is present.

A canister 1162 is arranged to receive therein a pulse echo UT transducer (not shown). The canister 1162 has a substantially planar surface 1164 arranged to attach the canister 1162 to the surface 16. For example, the surface 1164 may be adhered to the surface 16 with a suitable adhesive as desired for a particular application. An opening 1165 is defined in the canister 1162.

A surface 1166 of the canister 1162 defines a central hole with a slit 1168 extending radially outward therefrom. A push rod 1170 is received in the central hole. A tab 1172 extends radially outward from the push rod 1170. Inside the canister 1162 a plunger 1174 is attached to an end of the push rod 1170. A biasing device 1176 is interposed between the plunger 1174 and the surface 1166 of the canister 1162. For example, the biasing device 1176 may be a spring that is coiled around the push rod 1170 inside the canister 1162.

A pulse echo UT transducer (not shown) is placed in the canister 1162 through the opening 1165. The push rod 1170 is rotated as shown by an arrow 1178 until the tab 1172 aligns with the slit 1168. The biasing device 1176 urges the plunger 1174 and the push rod 1170 in a direction as shown by an arrow 1180. The plunger 1176 thus engages an upper portion of the pulse echo UT transducer and urges the pulse echo UT transducer against the surface 16 of the UUT 12.

Figure 2D:
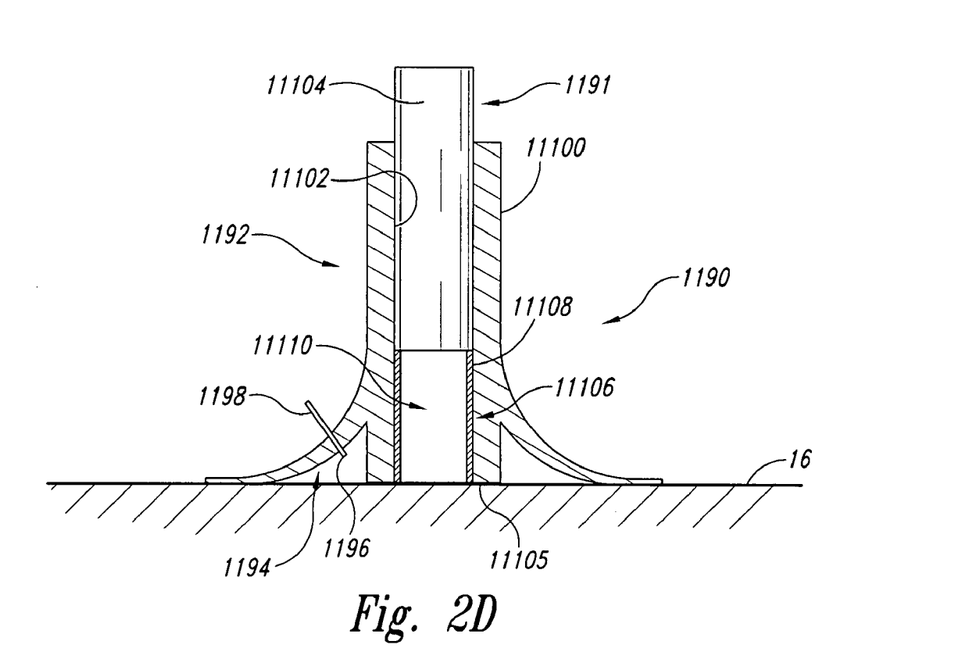
FIG. 2D is a cutaway side view of an exemplary focused beam pulse echo ultrasonic testing transducer mounted in an exemplary vacuum cup mount.

Referring now to FIG. 2D, a mount assembly 1190 can mount a focused pulse echo UT transducer 1191 to the surface 16 of the UUT 12. The mount assembly 1190 is held to the surface 16 of the UUT 12 using a vacuum (either temporary or continuous). The mount assembly 1190 is flexible, thereby allowing part deformation without affecting test results and minimizing separation issues under high strains. The mount assembly 1190 also does not entail being adhesively bonded to a surface of a part.

A vacuum cup 1192 has a suction ring 1194. The vacuum cup 1192 is suitably made of rubber. Thus, the mount assembly 1190 is flexible. The suction ring 1194 defines a vacuum port 1196. A vacuum line 1198 may be connected to the vacuum port 1196 to draw a continuous vacuum within the suction ring 1194 for mounting the vacuum cup 1192 to the surface 16 and maintaining the mount assembly 1190 continuously attached to the surface 16 via the continuous vacuum. For example, use of a continuous vacuum can help ensure that the mount assembly 1190 remains attached to the surface 16 throughout a mechanical test of the UUT 12. However, if desired the mount assembly 1190 may be attached to the surface 16 via a temporary vacuum. For example, the self-vacuum of the suction ring 1194 on the surface 16 can attach the mount assembly 1190 to the surface 16 for several hours.

A core 11100 of the vacuum cup 1192 extends from the suction ring 1194. The core 11100 has an inner cylindrical surface 11102. The inner cylindrical surface 11102 is sized to engage an outer cylindrical surface 11104 of the focused pulse echo UT transducer 1191, thereby maintaining the focused pulse echo UT transducer 1191 within the mount assembly 1190 via interference fit. A seal 11105 is disposed at an end of the core 11100 toward the suction ring 1194. The seal 11105 sealingly engages the surface 16 and seals the core 11100 from the surface 16 as vacuum holds the vacuum cup 1192 to the surface 16.

A stand-off sleeve 11106 has a cylindrical outer surface 11108. The stand-off sleeve 11106 maintains the focused pulse echo UT transducer 1191 spaced apart from the surface 16 of the UUT 12. The stand-off sleeve 11106 suitably is made of plastic or metal, as desired for a particular application. As such, the stand-off sleeve 11106 can give the mount assembly 1190 additional stiffness. The stand-off sleeve 11106 is received in the core 11100 toward the suction ring 1194. The inner cylindrical surface 11102 is sized to engage an outer cylindrical surface 11104 of the focused pulse echo UT transducer 1191, thereby maintaining the focused pulse echo UT transducer 1191 within the mount assembly 1191 via interference fit.

The stand-off sleeve 11106 helps ensure that the focal length of the focused pulse echo UT transducer 1191 is near the region where failure of the UUT 12 may first appear, thereby helping to increase sensitivity to any possible damage. The core 11100 is filled with an ultrasonic couplant 11110, such as without limitation water. The edge of the core 11100 is sealed at the seal 11105 by the vacuum at the surface 16 of the UUT 12, thereby helping to minimize any solid interfaces along the ultrasonic signal path that might contribute to reflections and signal losses. This is because there is only the ultrasonic couplant 11110 between the transducer and the part surface. The focused pulse echo UT transducer 1191 is slid into the core 11100, which has enough interference to provide a snug fit. It will be appreciated that any air bubbles in the core 11100 between the focused pulse echo UT transducer 1191 and the surface 16 should be removed. If desired, an optional, separate ultrasonic couplant inlet (not shown) and ultrasonic couplant outlet (not shown) may be provided if a particular mounting orientation (such as upside down) makes insertion of the ultrasonic couplant 10 and removal of any bubbles difficult.

Figure 2E:
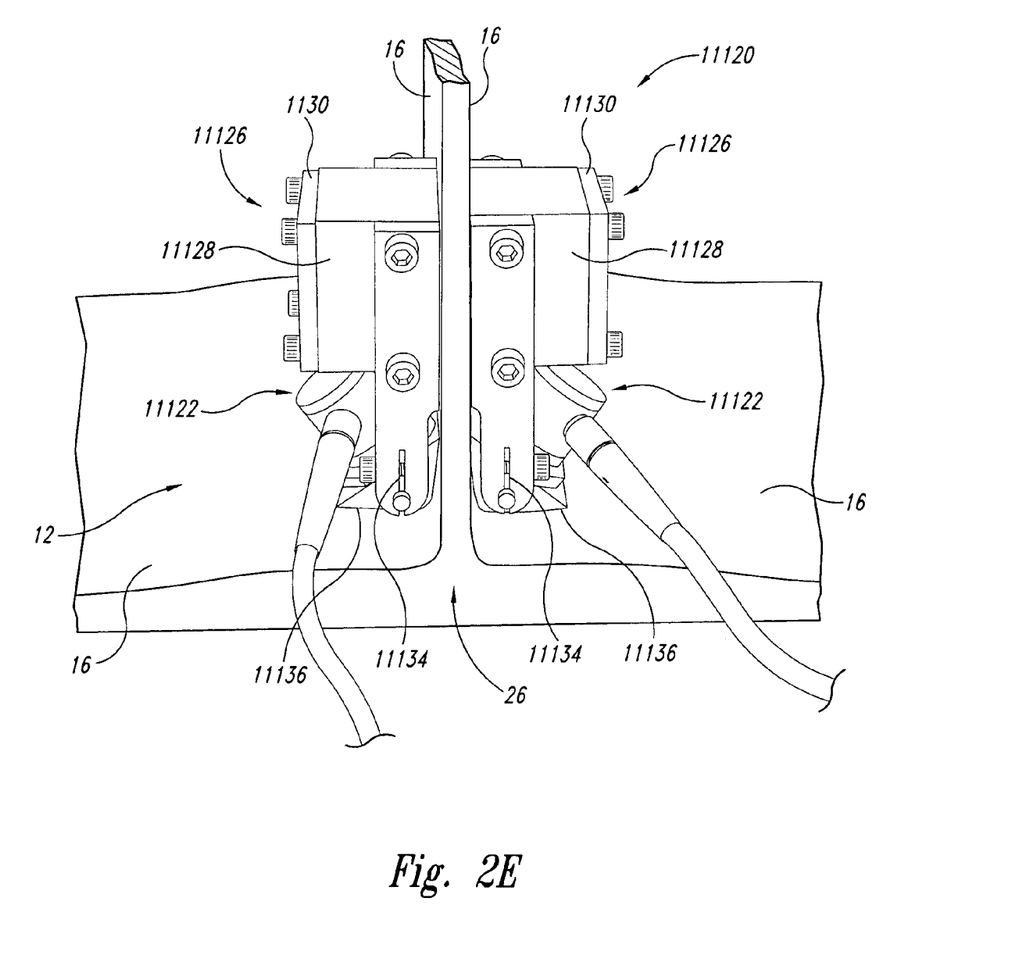
FIG. 2E is a side plan view of exemplary through transmission ultrasonic testing transducers mounted in an exemplary magnetic mount.

Referring now to FIG. 2E, a mount assembly 11120 can mount a pair of through transmission UT transducers 11122 to surfaces 16 of the UUT 12. The mount assembly 11120 magnetically mounts the through transmission UT transducers 11122 and is well-suited for enabling non-destructive inspection and monitoring of the joint 26 in the UUT 12.

The mount assembly 11120 includes a transducer mount 11126 for each of the through transmission UT transducers 11122. A magnet 11128 is installed in each transducer mount 11126, such as by being retained in place by a retaining frame 11130. The magnets 11128 are oriented relative to each other such that their domains are aligned to magnetically attract each other, thereby magnetically attaching each transducer mount 11126 to its respective surface 16 disposed therebetween near the joint 26.

A transducer mounting ring 11132 is attached to a mounting frame 11134 of each of the transducer mounts 11126. The transducer mounting ring 11132 receives therein the through transmission UT transducer 11122. In exemplary embodiments, the transducer mounting ring 11132 is attached to the mounting frame 11134 at any angle as desired for a particular application, such as for orienting the through transmission UT transducers to transmit and receive ultrasonic energy to and from the joint 26.

Wave guides 11136 ultrasonically couple ultrasonic energy between the through transmission UT transducers 11122 and the UUT 12. The wave guides 11136 may be made of any material that provides a medium having a suitable coefficient of transmission for the ultrasonic energy. Given by way of non-limiting example, the wave guides 11136 may be provided in the form of elastomeric stand-offs.

Referring back to FIG. 1, a multiplexer 28 is operatively coupled to the UT transducers 14. The multiplexer 28 can operate in pulse echo and through transmission modes. The multiplexer 28 can provide for multiplexed channel operation when combined with a standalone flaw detector, and can accommodate external triggering from a flaw detector. The multiplexer 28 may provide for individual gain and damping per channel. If desired, the multiplexer 28 may also provide for external channel addressing to control firing sequence of the UT transducers 14. Given by way of non-limiting example, the multiplexer 28 may be one or more eight channel multiplexers such as a Krautkramer MS-8 multiplexer available from GE Inspection Technologies.

The ultrasonic pulser/receiver 18 is operatively coupled to the multiplexer 28. Ultrasonic pulser/receivers are known to those of ordinary skill in the art and, as a result, details of their construction and operation are not necessary for an understanding. The ultrasonic pulser/receiver generates a pulse, such as a spike pulse or a square wave pulse, that is provided to the multiplexer 28. The multiplexer 28, in turn, may provide a gain adjust to the pulse or dampen the pulse, as desired. The multiplexer 28 then provides the gain-adjusted or dampened pulse to the UT transducers 14. The pulse width may be tunable as desired for a particular application, up to around 1000 ns, pulse repetition frequency of up to around 20 kHz may be provided, and pulse voltage may be adjustable from 50 V to around 450 V, as desired. The ultrasonic pulser/receiver 18 provides display capabilities, such as one or more A-scans as desired. The ultrasonic pulser/receiver 18 also provides outputs, such as analog outputs and transistor-transistor logic (TTL) outputs.

The ultrasonic pulser/receiver 18 suitably may be a flaw detector. In such a case, the multiplexer 28 is used in conjunction with the flaw detector to support multiplexed channel operation with more than one of the UT transducers 14. Given by way of non-limiting example, a suitable flaw detector may be a Krautkramer USN 60 portable ultrasonic flaw detector available from GE Inspection Technologies.

Alternately, the ultrasonic pulser/receiver 18 suitably may be a multi-channel ultrasonic testing instrument. When a multi-channel ultrasonic testing instrument is used, multiple UT transducers 14 can be coupled directly with the ultrasonic pulser/receiver 18. Thus, in such a case, the multiplexer 28 need not be provided. However, the multiplexer 28 optionally may be provided (for example, if a particular application calls for use of more UT transducers 14 than the number of channels available in the ultrasonic pulser/receiver 18). Given by way of non-limiting example, a suitable multi-channel ultrasonic testing instrument may be a Krautkramer USIP 40 multi-channel ultrasonic inspection instrument available from GE Inspection Technologies.

A mechanical test system and controller 30 of a test system embodiment causes the UUT 12 to be placed under mechanical loading. Systems for mechanically loading test structures are known to those of ordinary skill in the art, and details of their construction and operation are not necessary for an understanding of disclosed embodiments. Given by way of non-limiting examples, suitable mechanical test systems and controllers include a resonant fatigue tester machine, such as without limitation a Testronic Resonant Fatigue Tester, or a servohydraulic loading fatigue testing machine, such as without limitation an Instron Model 8502, or any suitably sized static and fatigue test systems as desired for a particular application, such as without limitation testing for large composite workpieces such as aircraft wings or sections, an aircraft fuselage or sections, or the like.

The computing system 20 is operatively coupled in data communication to the ultrasonic pulser/receiver 18 and to the mechanical test system and controller 30. In an exemplary embodiment, the computing system 20 and the ultrasonic pulser/receiver 18 may be operatively coupled by a high-speed data link, such as a network connection like an Ethernet connection or the like. Such a connection enables testing (that is, loading and ultrasonic sensing by the UT transducers 14) to be performed on the UUT 12 in one location while being monitored and controlled with the computing system 20 in a remote location. Remote location of the computing system 20 via such a connection avoids signal strength loss due to cable lengths or remote preamplifiers.

The computing system 20 includes a data acquisition system 22 that acquires data over time from the ultrasonic pulser/receiver 18 and controls the ultrasonic pulser/receiver 18. The data acquisition system 22 can acquire data that the ultrasonic pulser/receiver 18 provides as analog output and data that the ultrasonic pulser/receiver 18 provides as TTL output. The data acquisition system 20 can cause the acquired data to be stored or can provide access to the acquired data in real time for analysis.

The computing system also includes analysis software 32. Among other things, the analysis software 32 can organize and chart the acquired data, such as in a spreadsheet. The analysis software 32 can also analyze the acquired data for values that are indicative of failure or a flaw, such as a crack or delamination or disbond, in the UUT 12. In one embodiment, if the analysis software 32 detects initiation of failure (such as cracking or delamination or disbonding), the analysis software 32 can cause the computing system 20 to generate an alert or alarm, and/or can cause the computing system 20 to cause the mechanical test system and controller 30 to stop mechanically loading the UUT 12.

The analysis software 32 can analyze the acquired data from the data acquisition system 22 in real time as the data acquisition system 22 acquires the data from the ultrasonic pulser/receiver 18. The analysis software 32 can also access stored data that the data acquisition system 22 has caused to be stored. As such, testing can be performed (and data collected and stored) on a back shift and data can be analyzed as desired when appropriate personnel are available, thereby helping to increase the efficiency of use of equipment, facilities, and personnel.

A display 34 is operatively coupled to the computing system 20. The display 34 can display images generated by the data analysis software 32, either in real time or from stored data. The display 34 can also display images, such as one or more A-scans, in real time from data acquired by the data acquisition system 22.

Figure 3:
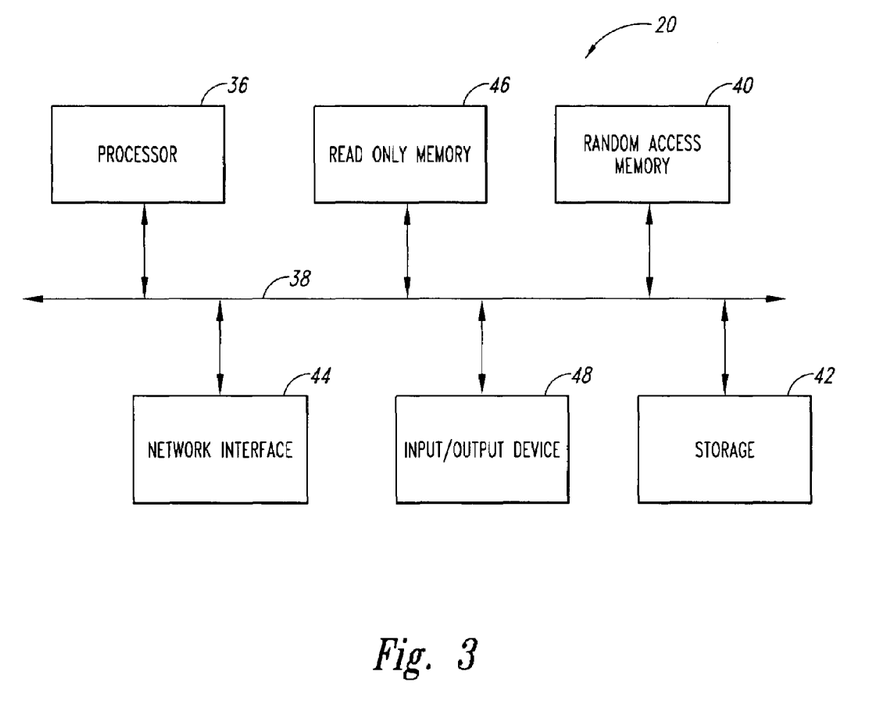
FIG. 3 is a block diagram of exemplary components of a computing system.

Referring now to FIG. 3, a typical computing system 20 (that also may be referred to as a host computer or system)

utilized in an embodiment includes a central processing unit ("CPU") (or microprocessor) 36 connected to a system bus 38. Random access main memory ("RAM") 40 is coupled to the system bus 38 and provides the CPU 36 with access to memory storage 42 for storing the acquired data and analyzed data. When executing program instructions, the CPU 36 stores those process steps in the RAM 40 and executes the stored process steps out of the RAM 40.

The computing system 20 connects to a computer network (not shown) via a network interface 44 and through a network connection (not shown), such as an Ethernet connection as discussed above. One such network is the Internet that allows the computing system 20 to download applications, code, documents and other electronic information.

Read only memory ("ROM") 46 is provided to store invariant instruction sequences such as start-up instruction sequences or basic input/output operating system (BIOS) sequences.

An Input/Output ("I/O") device interface 48 allows the computing system 20 to connect to various input/output devices, for example, a keyboard, a pointing device ("mouse"), a monitor, printer, a modem, and the like. The I/O device interface 48 is shown as a single block for simplicity and may include several interfaces to interface with different types of I/O devices.

It will be appreciated that embodiments are not limited to the architecture of the computing system 20 shown in FIG. 3. Based on the type of applications/business environment, the computing system 20 may have more or fewer components. For example, the computing system 20 can be a set-top box, a lap-top computer, a notebook computer, a desktop system, or other types of systems.

Figure 4:
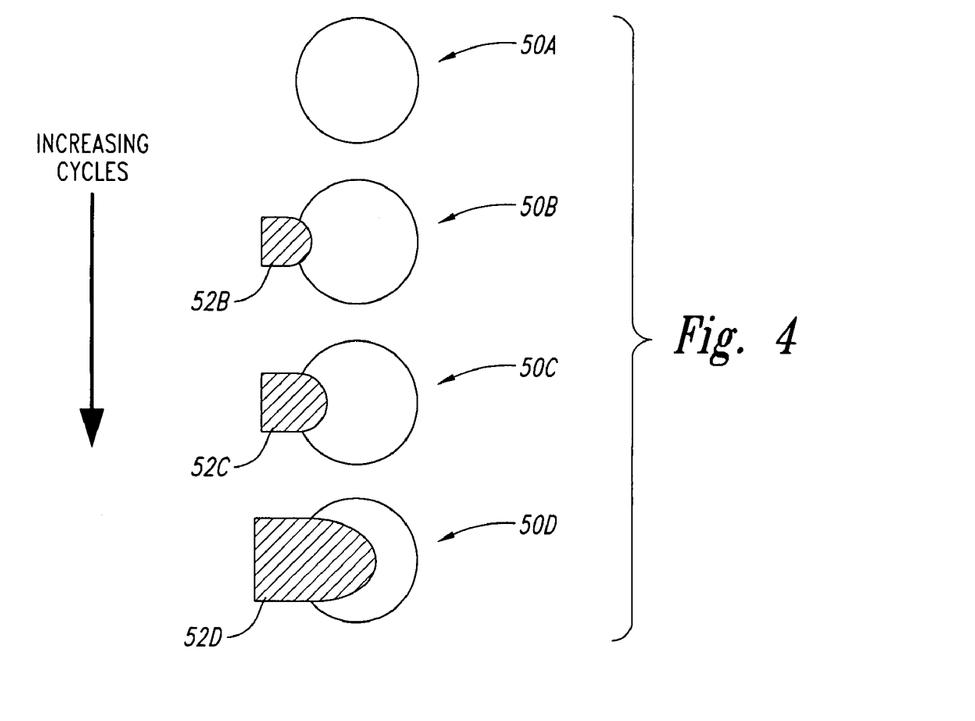
FIG. 4 illustrates failure growth in cross-sections of ultrasonic beams for increasing fatigue cycles.

Referring now to FIG. 4, growth of a failure mechanism is illustrated. Initially, no failure mechanism has initiated in an unloaded UUT 12 (not shown). Thus, no failure mechanism is detected in a cross section of an ultrasonic beam 50A. Therefore, no signal is reflected back to the UT transducer 14 (not shown).

With an increasing number of fatigue cycles induced in the UUT 12 (not shown) by the mechanical test system and controller 30 (not shown), a failure mechanism 52B, such as cracking or delamination or disbonding, initiates. The failure mechanism 52B covers a small portion of a cross section of an ultrasonic beam 50B. In previously-known, conventional methods of ultrasonic testing, initiation of failure was not detectable because a failure mechanism as small as the failure mechanism 52B could not be detected by a hand-held ultrasonic testing probe held by an operator onto a surface of an unloaded workpiece. However, according to exemplary embodiments, the slightest change in ultrasonic reflection, such as that change from the cross section of the ultrasonic beam 50A to the cross section of the ultrasonic beam 50B can be detected by the UT transducers 14 that are mounted to the surface 16 of the UUT 12. Further, according to exemplary embodiments, that slight, detectable change in ultrasonic reflection represents initiation of failure, such as by cracking or delamination or disbonding, of a composite structure under test. The analysis software 32 (FIG. 1) correlates the change in ultrasonic reflection (that indicates initiation of failure) back to time and load indicators, as defined by the mechanical test system and controller 30 (FIG. 1). As also discussed above, upon detection of the failure mechanism 52B the analysis software 32 can cause the computing system 20 to generate an alert or alarm, and/or can cause the computing system 20 to cause the mechanical test system and controller 30 to stop mechanically loading the UUT 12.

The failure mechanism grows as fatigue cycles increase. Failure mechanisms 52C and 52D cover increasingly larger portions of cross sections of ultrasonic beams 50C and 50D. For example, the failure mechanism 50D may cover around 50 percent or so of the cross section of the ultrasonic beam 50D. The failure mechanism 50D thus represents around the smallest failure mechanism that was previously detectable by a hand-held ultrasonic testing probe held by an operator onto a surface of an unloaded workpiece.

Figure 5:
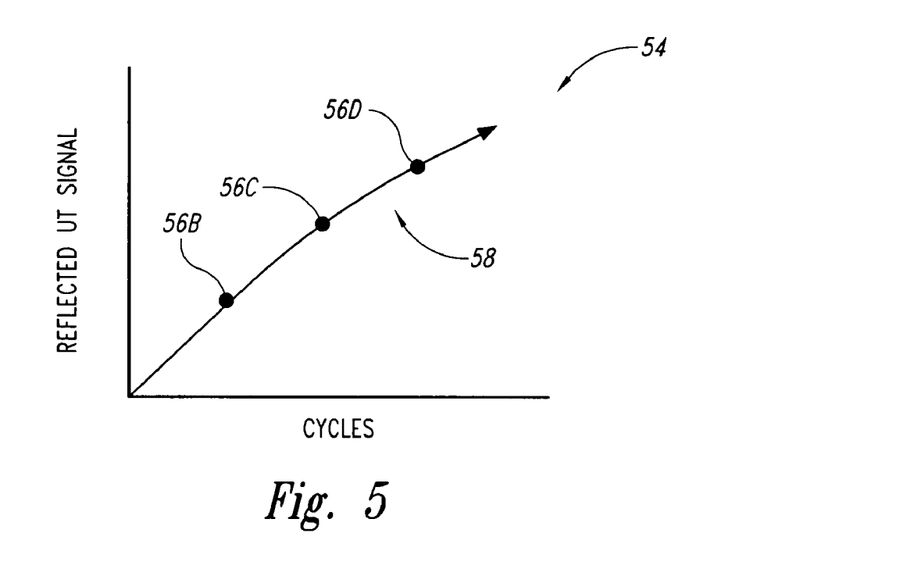
FIG. 5 is a graph of failure versus cycles.

Referring now to FIG. 5, the analysis software 32 (FIG. 1) can plot acquired data, thereby indicating initiation of and tracking growth of failures such as cracking or delaminations or disbondings. For example, a graph 54 plots UT signals versus fatigue cycles. A point 56B can plot the failure mechanism 52B, thereby indicating initiation of failure. Points 56C and 56D can plot the failure mechanisms 52C and 52D, thereby tracking growth of failure. A curve 58 can be fitted through the points 56B, 56C, and 56D.

Figure 6:
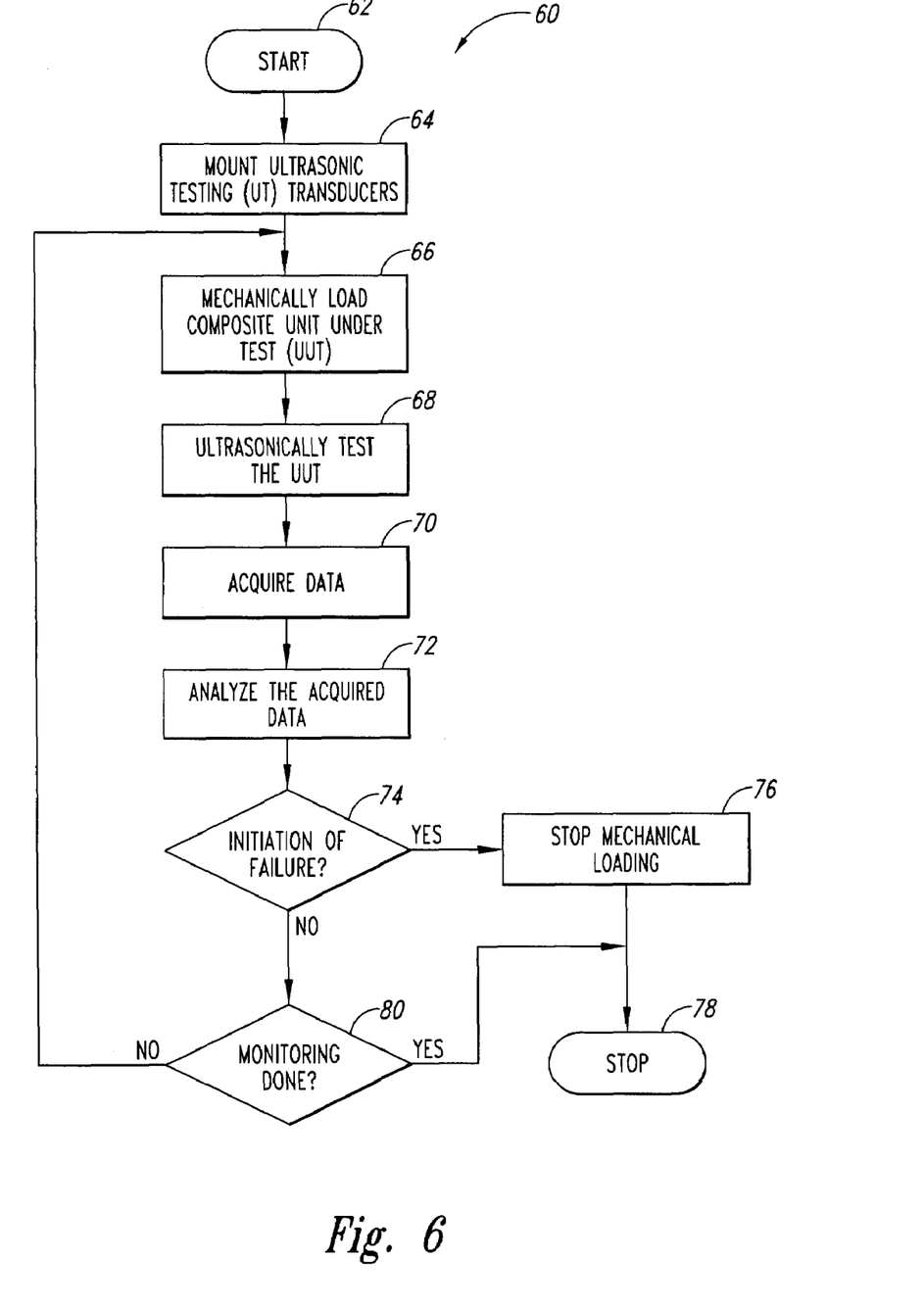
FIG. 6 is a flowchart of an exemplary method for monitoring a composite workpiece.

Referring now to FIG. 6, a method 60 can provide for automated monitoring of a composite workpiece or unit under test (UUT). The method 60 suitably is implemented with the inspection system 10 (FIG. 1) in conjunction with the mechanical test system and controller 30 (FIG. 1), as described above. For purposes of brevity, details described above will not be repeated. The method 60 starts at a block 62.

At a block 64 ultrasonic testing (UT) transducers are mounted to a surface of a UUT. The UT transducers may be mounted in mounts as desired for a particular application and as determined by space constraints and presence of any interference. The UT transducers may be pulse echo UT transducers, such as flat beam pulse echo UT transducers or focused beam pulse echo UT transducers, as desired. The UT transducers may also be through transmission UT transducers as desired for a particular application, such as inspection of a joint. Any combination of one or more types of UT transducers may be used. In addition, the UT transducers may be mounted in any arrangement as desired. For example, the UT transducers may be arranged and mounted in a line or a matrix for tracking growth of failure such as cracking or delamination or disbonding.

At a block 66 the UUT is mechanically loaded. For example, a mechanical test system and controller can begin inducing fatigue cycles in the UUT.

At a block 68, the UUT is ultrasonically tested or inspected by the UT transducers mounted thereon while the UUT is mechanically loaded. A transmit electrical signal, such as a spike or aquare wave, is generated by an ultrasonic pulser/receiver. The transmit electrical signal (which may be multiplexed, as discussed above) is transmitted to the UT transducers. At each UT transducer a stress wave is sent into the UUT from the UT transducer and a reflected stress wave is received at the UT transducer. The stress wave is converted to a receive electrical signal. The receive electrical signal (which may be multiplexed, as discussed above) is sent from the UT transducers to the ultrasonic pulser/receiver for processing.

At a block 70, data indicative of ultrasonically testing the UUT is acquired from the ultrasonic pulser/receiver. The acquired data may be stored for later analysis, if desired.

At a block 72, the acquired data is analyzed. As discussed above, the acquired data may be analyzed in real time. Alternately, as discussed above, acquired data that had been stored may be retrieved from storage and the retrieved data can be analyzed later when desired. The acquired data can be analyzed for initiation of failure, such as cracking or delamination or disbonding. The acquired data can also be analyzed for growth of failure, such as cracking or delamination or disbonding.

At a decision block 74, a determination is made if initiation of failure has been detected. If initiation of failure is detected, then in one embodiment at a block 76 mechanical loading can be stopped. In addition, an alarm or warning can be generated, if desired. The method 60 can then stop at a block 78. However, in another embodiment, testing can continue after failure initiation. For example, other locations can be monitored for failure initiation.

If initiation of failure is not detected at the decision block 74, then at a decision block 80 a determination is made whether monitoring of the UUT is done. If so, then the method 60 stops at the block 78. If not, then the method returns to the block 66 and monitoring of the loaded UUT continues as desired.

While a number of exemplary embodiments and aspects have been illustrated and discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A system for in-situ monitoring of a composite workpiece, the system comprising:
    at least one ultrasonic testing transducer mounted to a surface of a composite workpiece to transmit and receive ultrasonic energy to and from the composite workpiece during mechanical loading of the composite workpiece;
    an ultrasonic pulser and receiver operatively coupled to the at least one ultrasonic testing transducer; and
    a computing system operatively coupled to the ultrasonic pulser and receiver, the computing system including:
        a data acquisition component to acquire data from the ultrasonic pulser and receiver during the mechanical loading; and
        a data analysis component to analyze the acquired data during the mechanical loading, by
            identifying a change in an ultrasonic reflection included in the ultrasonic energy received from the composite workpiece during the mechanical loading wherein the change in the ultrasonic reflection indicates initiation of a failure mechanism of the composite workpiece; and
            upon identifying the change in the ultrasonic reflection, signaling detection of the failure mechanism during the mechanical loading.

2. The system of claim 1, further comprising a multiplexer operatively coupled between the ultrasonic pulser and receiver and the at least one ultrasonic testing transducer.

3. The system of claim 1, further comprising storage media configured to store the acquired data.

4. The system of claim 1, wherein the computing system is operatively coupled to the ultrasonic pulser and receiver via a high-speed data link.

5. The system of claim 4, wherein the high-speed data link includes a network connection.

6. The system of claim 1, wherein the at least one ultrasonic testing transducer includes an ultrasonic testing transducer chosen from a pulse echo ultrasonic testing transducer and a pair of through transmission ultrasonic testing transducers.

7. The system of claim 1, wherein the data analysis component is further configured to analyze the acquired data to monitor the change in the ultrasonic reflection to monitor growth of the failure mechanism of the composite workpiece.

8. The system of claim 7, wherein the data analysis component is further configured to plot the growth of the failure mechanism of the composite workpiece versus a plurality of fatigue cycles during the mechanical loading of the composite workpiece.

9. The system of claim 1, wherein the at least one ultrasonic testing transducer includes a plurality of ultrasonic testing transducers mounted to the surface of a composite workpiece and arranged in an array.

10. The system of claim 1, wherein the data analysis component is further configured to stop the mechanical loading of the composite workpiece after the detection of the failure mechanism.

11. The system of claim 1, wherein the failure mechanism includes cracking of the composite workpiece.

12. The system of claim 1, wherein the failure mechanism includes debonding of the composite workpiece.

13. The system of claim 1, wherein the failure mechanism includes delaminating of the composite workpiece.

14. The system of claim 1, wherein the data analysis component is further configured to identify a lack of an ultrasonic reflection included in the ultrasonic energy received from the composite workpiece during the mechanical loading as indicating no failure mechanism is detected.

15. A system for testing a composite workpiece, the system comprising:
    a mechanical test system and controller configured to cause a composite workpiece to be placed under mechanical load to cause initiation and growth of a failure mechanism in the composite workpiece;
    at least one ultrasonic testing transducer mounted to the surface of a composite workpiece and configured to transmit and receive ultrasonic energy to and from the composite workpiece during mechanical loading of the composite workpiece;
    an ultrasonic pulser and receiver operatively coupled to the at least one ultrasonic testing transducer; and
    a computing system operatively coupled to the mechanical test system and controller and to the ultrasonic pulser and receiver, the computing system including:
        a data acquisition component configured to acquire data representing reflections of pulses of ultrasonic energy from the composite workpiece during the mechanical loading; and
        a data analysis component configured to analyze the acquired data during the mechanical loading, wherein the data analysis component is configured to:
            identify a change in the reflections of the pulses of ultrasonic energy received from the composite workpiece during the mechanical loading, wherein the change in the reflections of the pulses of ultrasonic energy indicates a change in size of the failure mechanism; and
            track the change in size of the failure mechanism.

16. The system of claim 15, further comprising storage media configured to store the acquired data.

17. The system of claim 15, wherein the computing system is operatively coupled to the ultrasonic pulser and receiver via a high-speed data link.

18. The system of claim 17, wherein the high-speed data link includes a network connection.

19. The system of claim 15, wherein the at least one ultrasonic testing transducer includes an ultrasonic testing transducer chosen from a pulse echo ultrasonic testing transducer and a pair of through transmission ultrasonic testing transducers.

20. The system of claim 15, wherein the computing system further includes a control component configured to automatically cause the mechanical test system and controller to stop causing the composite workpiece to be placed under mechanical load responsive to detection by the data analysis component of initiation of the failure mechanism in the composite workpiece.

21. The system of claim 15, wherein the at least one ultrasonic testing transducer includes a plurality of ultrasonic testing transducers mounted to the surface of a composite workpiece and arranged in an array.

22. A method for monitoring a composite workpiece, the method comprising:
   mechanically loading a composite workpiece by inducing a plurality of fatigue cycles in the composite workpiece; and
   during mechanical loading of the composite workpiece:
      ultrasonically testing the composite workpiece with at least one ultrasonic testing transducer mounted to a surface of the composite workpiece; wherein the at least one ultrasonic testing transducer generates pulses of ultrasonic energy through a cross section of the composite workpiece;
      acquiring data representing reflections of the pulses of ultrasonic energy from the cross section of the workpiece, wherein changes in the reflections of the pulses of ultrasonic energy are indicative of changes in the cross section of the workpiece representing one of initiation of a failure mechanism and a growth of the failure mechanism in the composite workpiece; and
      analyzing the acquired data to:
         identify the changes in the reflections of the pulses of ultrasonic energy received from the composite workpiece; and
         track the changes in the reflections of the pulses of ultrasonic energy to track at least one of the initiation of the failure mechanism and the growth of the failure mechanism with increasing fatigue cycles.

23. The method of claim 22, further comprising mounting the at least one ultrasonic testing transducer to the surface of the composite workpiece.

24. The method of claim 23, wherein mounting the at least one ultrasonic testing transducer to the surface of the composite workpiece includes arranging a plurality of ultrasonic testing transducers on the surface of the composite workpiece in an array.

25. The method of claim 22, wherein ultrasonically testing includes:
   transmitting a transmit electrical signal to the at least one ultrasonic testing transducer;
   sending at least one stress wave into the composite workpiece from the at least one ultrasonic testing transducer;
   receiving at least one reflected stress wave at the at least one ultrasonic testing transducer; and
   converting the at least one reflected stress wave to at least one receive electrical signal.

26. The method of claim 25, further comprising multiplexing the at least one transmit electrical signal and multiplexing the at least one receive electrical signal.

27. The method of claim 22, further comprising storing the acquired data.

28. The method of claim 27, further comprising:
   retrieving the stored data; and
   analyzing the retrieved data.

29. The method of claim 22, further comprising automatically stopping mechanical loading of the composite workpiece responsive to detection of the failure mechanism of the composite workpiece.

* * * * *